United States Patent

Klein et al.

[11] Patent Number: 5,585,520
[45] Date of Patent: Dec. 17, 1996

[54] PROCESS FOR THE PREPARATION OF O-SUBSTITUTED HYDROXYLAMMONIUM SALTS

[75] Inventors: Ulrich Klein, Limburgerhof; Ernst Buschmann, Ludwigshafen; Michael Keil, Freinsheim; Norbert Götz, Worms; Albrecht Harreus, Ludwigshafen, all of Germany

[73] Assignee: BASF Aktiengesellschaft, Ludwigshafen, Germany

[21] Appl. No.: 592,351

[22] PCT Filed: Jul. 8, 1994

[86] PCT No.: PCT/EP94/02239

§ 371 Date: Jan. 11, 1996

§ 102(e) Date: Jan. 11, 1996

[87] PCT Pub. No.: WO95/04032

PCT Pub. Date: Feb. 9, 1995

[30] Foreign Application Priority Data

Jul. 31, 1993 [DE] Germany .................. 43 25 851.4

[51] Int. Cl.$^6$ .................................. C07C 213/00
[52] U.S. Cl. .................. 564/300; 548/561; 549/74; 549/426
[58] Field of Search .................. 564/300; 548/561; 549/74, 426

[56] References Cited

U.S. PATENT DOCUMENTS 5,382,685 1/1995 Klein et al. .................. 564/301

FOREIGN PATENT DOCUMENTS

| 1296022 | 2/1992 | Canada . |
| 243595 | 9/1985 | Czechoslovakia . |
| 259850 | 3/1988 | European Pat. Off. . |
| 3631071 | 3/1988 | Germany . |
| 4233333 | 4/1994 | Germany . |

OTHER PUBLICATIONS

*Liebigs Am. Chem.*, vol. 257, pp. 203–247, Mar. 1890.
*J. Am. Chem. Soc.*, vol. 58, pp. 2020–21, 1936.
*J. of Chem. Soc.*, pp. 182–186, 1948.
*Heterocycles*, vol. 20, pp. 839–843, 1983.
*Houben–Weyl, Methoden der Org. Chem.*, vol. 10/4, 4th Ed., 1968, pp. 265–273.
*Chem. Abst.*, vol. 109, 1988, Abs. No. 8922s (Abstract of CS–A 243 595).
*Houben–Weyl, Methoden der Org. Chem.*, vol. 10/1, 4th Ed., 1971, p. 1186.
*Org. Synth. Coll.*, vol. 3, p. 172.

*Primary Examiner*—Peter O'Sullivan
*Attorney, Agent, or Firm*—Keil & Weinkauf

[57] ABSTRACT

Preparation of O-substituted hydroxylammonium salts I

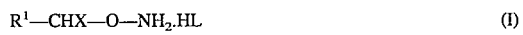

(L=halogen, hydrogensulfate; X=H, alkyl; $R^1$=unsubst. or subst. phenyl, thienyl, furanyl, pyrrolyl or —$CR^2$=$CR^3R^4$; $R^2$, $R^3$, $R^4$=H, halogen or alkyl) by reaction of an acetone oxime O-allyl or —O—benzyl ether II

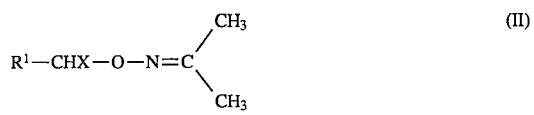

with water and a mineral acid H—L with continuous removal of the acetone formed in this process, by carrying out the hydrolysis batchwise at 0°–50° C. and under a pressure of 10–500 mbar is described.

The O-substituted hydroxylammonium salts I are intermediates for plant protection agents and pharmaceuticals.

3 Claims, No Drawings

PROCESS FOR THE PREPARATION OF O-SUBSTITUTED HYDROXYLAMMONIUM SALTS

This application is a 371 of PCT/EP94/02239, filed 8 Jul. 1994.

The present invention relates to an improved process for preparing O-substituted hydroxylammonium salts of the general formula I

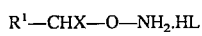

where L is halogen or hydrogensulfate, X is hydrogen or $C_1$–$C_4$-alkyl and $R^1$ is phenyl, thienyl, furanyl or pyrrolyl which, if desired, are substituted or a radical —$CR^2$=$CR^3R^4$, $R^2$, $R^3$ and $R^4$ independently of one another being hydrogen, halogen or $C_1$–$C_4$-alkyl,
by reaction of an acetone oxime ether of the formula II

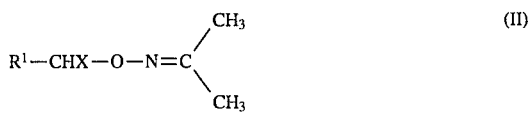

with water and a mineral acid H—L with continuous removal of the acetone formed in this process.

O-Substituted hydroxylamines can be prepared, inter alia, by acidic hydrolysis of O-substituted acetone oxime ethers at boiling point. For example, DE-A 36 31 071 thus discloses a process for hydrolyzing acetone oxime ethers of the compound II type with hydrochloric acid, which is carried out in a continuously operated reaction column. For this purpose, however, an expensive special apparatus is necessary.

Substantially more economical processes are those, however, which can be carried out in standard apparatuses:

For example, Behrend et al. (Liebigs Ann. Chem. 257 (1890), 203), prepared benzyloxyamine hydrochloride in 50% yield.

Borek et al. (J. Am. Chem. Soc. 58 (1936), 2020) synthesized carboxymethylenoxyamine hydrochloride in 50% yield.

Holland et al. (J. Chem. Soc. 1948, 182) obtained diethylaminoethylenoxyamine according to this method, but they do not indicate any yield.

Brossi et al. (Heterocycles 20 (1983), 839) obtained 3'-(2,4,5-trichlorophenoxy)propyloxyamine hydrochloride by hydrolysis of the corresponding acetone oxime ether in ethanolic hydrochloric acid. The yield, however, was only 47%.

A disadvantage of these known processes, however, is the unsatisfactory purity of the products. The interfering by-products result mainly from the partial decomposition of the desired hydroxylamine derivatives under the reaction conditions required (for this also see Zech and Metzget in Houben-Weyl, Methoden der Organischen Chemie (Methods of Organic Chemistry), Vol. 10/1, 4th Edition 1971, p. 1186). Apart from the additional purification step, the processes are also not very viable industrially because of the low yield of the product of value.

The earlier German Application DE-A 42 33 333 describes a process for the synthesis of O-alkylhydroxylammonium salts containing short-chain alkyl radicals. The hydrolysis of the acetone oxime ether is carried out here using concentrated hydrochloric acid in a two-phase system using nonpolar solvents such as xylene, toluene and cyclohexane. This process is suitable, however, only for the synthesis of relatively polar O-alkylhydroxylammonium salts. It is not suitable for the synthesis of the less polar compounds II, which would dissolve in the solvent. The reaction times in this case are very long due to phase transition.

Org. Synth., Coll. Vol. 3, p. 172 discloses the hydrolysis of acetone oxime O-(methoxycarbonylmethylene) ether with aqueous hydrochloric acid with simultaneous removal of the by-product acetone by distillation. Hydrolysis is carried out at 100° C. The yields are 66–72%. This method, however, is also not suitable for the synthesis of the compounds I, as the O—allyl— and O-benzyl-substituted hydroxylammonium salts I are not stable at above 50° C. As a result of cleavage of the N—O bond, ammonium chloride would be formed as a by-product, which would only have to be separated off again in a subsequent purification step. At above 100° C., the decomposition of the compounds II can even take place explosively. A high yield of I can in any case not be achieved according to this process.

It was therefore the object of the present invention to provide an improved process with which the O-substituted hydroxylammonium salts I can be prepared in good yield and with very high purity.

Accordingly the present process has been found, which comprises carrying out the hydrolysis batchwise at 0°–50° C. and under a pressure of 10–500 mbar.

The reaction is particularly advantageously carried out at a reaction temperature from 30° to 50° C. and a pressure from 40 to 50 mbar.

According to present knowledge, it is expedient to employ approximately 2 molar equivalents of mineral acid per molar equivalent of acetone oxime ether II. A large excess of H—L is possible, but conveys no advantages.

Suitable mineral acids H—L are particularly hydrochloric acid and sulfuric acid, concentrated hydrochloric acid being particularly preferred.

The present process is advantageously carried out in the liquid phase, it also being possible to add an inert, highly water-miscible solvent, e.g. a lower alcohol such as methanol, ethanol and propanol, or a short-chain carboxylic acid such as acetic acid and propionic acid.

The amounts of solvent and mineral acid H—L are not critical. Normally, the process is carried out using a 5 to 100-fold molar excess of water and a 30–200% molar excess of H—L, based on the acetone oxime ether II.

The progress of the reaction can be monitored by means of customary analytical methods such as thin-layer chromatography, high-pressure liquid chromatography and gas chromatography.

After reaction is complete and the hydrolysis by-product acetone has been largely removed, customarily by distillation, the remaining water and the excess mineral acid H—L are removed, expediently by azeotropic distillation. Suitable water-entraining agents for this purpose are generally all organic solvents which form azeotropes with water, ie., for example, benzene, toluene, xylene, pentane, hexane, heptane, cyclohexane and cycloheptane.

Normally, the product I (H—L salt) crystallizes out from the residue and can then be isolated by means of customary methods, such as filtration or extraction (e.g. with water or alcohols) and, if desired, further purified, e.g. by crystallization, rectification or by means of chromatographic methods.

The acetone oxime ethers II used as starting substances are known or obtainable in a known manner (cf., for example, Houben-Weyl, Methoden der Organischen Chemie (Methods of Organic Chemistry), Volume X/4, Georg Thieme Verlag, Stuttgart 1968, pages 217ff).

The process can be used successfully for the synthesis of all O-substituted hydroxylammonium salts I as defined, especially for those compounds where the variables have the following meanings:

L is chlorine, bromine or hydrogensulfate, in particular chlorine;

X is hydrogen or $C_1$–$C_4$-alkyl, in particular hydrogen;

$R^1$ is phenyl, thienyl, furanyl or pyrrolyl, each of which can be unsubstituted or can carry one to three halogen atoms and/or $C_1$–$C_4$-alkyl radicals, in particular fluorine, chlorine, bromine, methyl or ethyl;

a radical —$CR^2$=$CR^3R^4$, $R^2$, $R^3$ and $R^4$ each being hydrogen, halogen such as fluorine, chlorine or bromine, or $C_1$–$C_4$-alkyl, in particular chlorine or methyl;

phenyl, halophenyl, thienyl and —CH=CH—Cl are particularly preferred, —CH=CH—Cl being very particularly preferred.

With respect to the use of the O-substituted hydroxylammonium salts I as intermediates for crop protection agents and pharmaceuticals, in particular for preparing herbicidal cyclohexenone oxime ethers (cf., for example, EP-A 136 647, EP-A 136 702 and EP-A 142 741), the preparation of O-benzylhydroxylammonium salts from acetone oxime O-benzyl ether and in particular of E-(O)-(3-chloro-2-propenyl)hydroxylammonium salts from E-acetone oxime O-(3-chloro-2-propenyl) ether is very particularly preferred.

PREPARATION EXAMPLES

Example 1 (according to the invention): O-benzylhydroxylamine hydrochloride

A mixture of 198.6 g (1.0 mol) of acetone oxime O-benzyl ether (purity: 82%) and 200 g (2.0 mol) of 36% strength by weight hydrochloric acid was distilled at a bottom temperature of 50° C., a pressure of 40 - 35 mbar and a reflux ratio of 6 through a column 30 cm long, which was packed with glass Raschig rings. After distilling off about 60 g of a mixture of dilute hydrochloric acid and acetone, the residue was treated with 500 ml of toluene. A further 120 g of hydrochloric acid were then distilled off at a bottom temperature of 50° C. and a pressure of 20–30 mbar. The solid O-benzylhydroxylamine hydrochloride was separated off and dried at 50° C. under reduced pressure. Yield: 172.5 g (94%; 88% purity)

Example 2 (according to the invention): E-(O)-(3-chloro-2-propenyl)hydroxylamine hydrochloride A mixture of 158.3 g (1.0 mol) of (E)-acetone oxime O-(3-chloro-2-propenyl) ether (purity: 91%) and 200 g (2.0 mol) of 36% strength by weight hydrochloric acid was distilled at a bottom temperature of 40°–50° C., a pressure of 40–50 mbar and a reflux ratio of 6 through a column 30 cm long, packed with glass Raschig rings. In the course of 15 hours, 145 g of a mixture of dilute hydrochloric acid and acetone were distilled off. During the distillation, the hydroxylamine hydrochloride crystallized out from the reaction mixture. After addition of 500 ml of cyclohexane, the remaining hydrochloric acid was distilled off azeotropically at 40°–45° C. and a pressure of 250 - 240 mbar, after which the solid E-(O)-(3-chloro-2-propenyl)hydroxylamine hydrochloride was separated off and dried at 50° C. under reduced pressure for 12 hours. The residue still contained 14.5 g (0.1 mol) of E-acetone oxime O-(3-chloro-2-propenyl) ether. Yield: 116 g (90%; 98% purity); m.p.: 175°–176° C.

Example 3 (according to the invention): E-(O)-(3-chloro-2-propenyl)hydroxylamine hydrochloride A mixture of dilute hydrochloric acid and acetone was distilled off at a bottom temperature of 45°–49° C., a pressure of 40–50 mbar and a reflux ratio of 6 from a mixture of 23.0 kg (144.8 mol) of acetone oxime O-(3-chloro-2-propenyl) ether (purity: 91%) and 30.0 kg (205 mol) of 36% strength by weight hydrochloric acid. For working up, the reaction mixture was treated with 45 l of toluene, after which the remaining hydrochloric acid was distilled off azeotropically at 43° C. and a pressure of 50–60 mbar. The E-(O)-(3-chloro-2-propenyl)hydroxylamine hydrochloride remaining as the crude product was separated off and dried under reduced pressure at 50° C. Yield: 16.0 kg (75%; 98% purity); m.p.: 176°–178° C.

Elemental analysis:

Calc.: C: 25.02; H: 5.00; O: 11.11; N: 9.73; Cl: 49.24; Found: C: 24.90; H: 4.90; O: 11.80; N: 9.70; Cl: 48.80.

Example 4 (Comparison example, similar to Org. Synth., Coll. Vol. 3, p. 172): E-(O)-(3-chloro-2-propenyl)hydroxylamine hydrochloride A mixture of 158.3 g (1.0 mol) of 91% (E)-acetone oxime O-(3-chloro-2-propenyl) ether and 200 g (2.0 mol) of 36% strength by weight hydrochloric acid was distilled through a 30 cm column which is packed with glass Raschig rings at a bottom temperature of 68°–69° C., at 165–200 mbar and a reflux ratio of 16. In the course of 15 hours, 145 g of a mixture of dilute hydrochloric acid and acetone were thus obtained. The hydroxylamine hydrochloride crystallized out from the residue. For working up, the residue was treated with 500 ml of cyclohexane and the remaining hydrochloric acid was distilled off azeotropically at 40°–45° C. and 250 - 240 mbar.

The solid E-(O)-(3-chloro-2-propenyl)hydroxylamine hydrochloride was separated off and dried under reduced pressure at 50° C. for 12 hours. Yield: 100 g (69%; 80% purity); m.p.: 160°–162° C.

According to $^1$H-NMR spectrum, the product still contained 20% by weight of ammonium chloride.

Example 5 (Comparison example, according to DE-A 42 33 333): E-(O)-(3-chloro-2-propenyl)hydroxylammonium chloride A mixture of 73.8 g (0.5 mol) of E-acetone oxime-O-(3-chloro-2-propenyl) ether, 1 l of cyclohexane and 76 g (0.75 mol) of 36% strength by weight hydrochloric acid was distilled through a column of 30 cm length which is packed with glass Raschig rings at a bottom temperature of 72°–75° C. and a reflux ratio of 6, a further 1900 ml of cyclohexane and a further 150 g (1.5 mol) of 36% strength by weight hydrochloric acid being added during the distillation. After 25 hours, 1935 g of distillate had collected in this way. The remaining hydrochloric acid was distilled off azeotropically from the residue after addition of cyclohexane, after which crystallized E-(O)-(3-chloro-2-propenyl)hydroxyammonium chloride was separated off. Yield: 36.1 g (40%; 80% purity); m.p.: 160°–162° C.

According to $^1$H-NMR spectrum, the product still contained 20% by weight of ammonium chloride.

Preparation of the precursors:

Acetone oxime O-benzyl ether 292 g (4.0 mol) of acetone oxime were added to a solution of 352 g (8.8 mol) of sodium hydroxide in 2 kg of water in a 4 l reaction vessel. The mixture was then heated to 70°–75° C. and treated with 506 g (4.0 mol) of benzyl chloride. After stirring for 3 hours at 75°–80° C., the reaction mixture was cooled, after which the organic phase was separated off and dried. Yield: 579 g (73%; 82% purity).

E-Acetone oxime O-(3-chloro-2-propenyl) ether 14.5 kg of 25% strength by weight aqueous hydroxylammonium sulfate solution (=22 mol of hydroxylammonium sulfate) and 10 kg of water were treated gradually in a 50 l reaction vessel with a total of 2.9 kg (50 mol) of acetone and 2.5 l of 50% strength by weight sodium hydroxide solution. The addition was carried out such that the pH of the reaction mixture was constantly at from 4.5 to 5.0. After addition was complete, the mixture was stirred for a further 2 hours and then treated with a further 5.28 kg (66 mol) of 50% strength by weight sodium hydroxide solution. The mixture was then heated to 70° C. and 5.09 kg (44 mol) of E-1,3-dichloropropene was added to the reaction mixture, after which it was stirred at 70°–80° C. for three hours. By distillation at a reduced pressure of 140 mbar and a transition temperature of 25°–53° C., a two-phase distillate was obtained whose organic phase contained the product. Yield: 5.0 kg (76%; 91% purity).

We claim:

1. A process for preparing O-substituted hydroxylammonium salts of the general formula I

R¹—CHX—O—NH₂.HL     (I)

where L is halogen or hydrogensulfate, X is hydrogen or $C_1$–$C_4$-alkyl and R¹ is phenyl, thienyl, furanyl or pyrrolyl which, if desired, are substituted or a radical —CR²=CR³R⁴, R², R³ and R⁴ independently of one another being hydrogen, halogen or $C_1$–$C_4$-alkyl, by reaction of an acetone oxime ether of the formula II

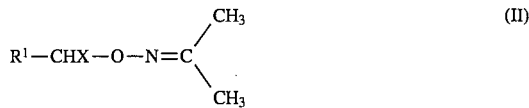

with water and a mineral acid H—L with continuous removal of the acetone formed in this process, which comprises carrying out the hydrolysis batchwise at 0°–50° C. and under a pressure of 10–500 mbar.

2. A process as claimed in claim 1, which is used for the preparation of E-(O)-(3-chloro-2-propenyl)hydroxylammonium salts from E-acetone oxime O-(3-chloro-2-propenyl) ether or of O-benzylhydroxylammonium salts from acetone oxime O-benzyl ether.

3. A process as claimed in claim 1, which is used for the preparation of E-(O)-(3-chloro-2-propenyl)hydroxylammonium salts from E-acetone oxime O-(3-chloro-2-propenyl) ether.

* * * * *